United States Patent
Wu et al.

(10) Patent No.: US 9,241,904 B1
(45) Date of Patent: Jan. 26, 2016

(54) METHOD FOR PREPARING METERED DOSE SPRAYED INHALER FOR TREATING RESPIRATORY DISEASE

(75) Inventors: Wei-Hsiu Wu, Taipei (TW); Yen-Chin Chao, Taipei (TW)

(73) Assignee: INTECH BIOPHARM LTD., Taipei (TW)

(*) Notice: Subject to any disclaimer, the term of this patent is extended or adjusted under 35 U.S.C. 154(b) by 74 days.

(21) Appl. No.: 14/239,722

(22) PCT Filed: Feb. 14, 2012

(86) PCT No.: PCT/CN2012/071129
§ 371 (c)(1),
(2), (4) Date: Feb. 19, 2014

(87) PCT Pub. No.: WO2013/026269
PCT Pub. Date: Feb. 28, 2013

(30) Foreign Application Priority Data

Aug. 19, 2011 (CN) .......................... 2011 1 0239124

(51) Int. Cl.
| | |
|---|---|
| A61K 9/00 | (2006.01) |
| A61K 31/4704 | (2006.01) |
| A61K 31/58 | (2006.01) |
| A61K 47/10 | (2006.01) |
| A61K 31/56 | (2006.01) |
| A61K 31/573 | (2006.01) |
| B65B 3/00 | (2006.01) |

(52) U.S. Cl.
CPC ............. *A61K 9/008* (2013.01); *A61K 31/4704* (2013.01); *A61K 31/56* (2013.01); *A61K 31/573* (2013.01); *A61K 31/58* (2013.01); *A61K 47/10* (2013.01); *B65B 3/003* (2013.01)

(58) Field of Classification Search
None
See application file for complete search history.

(56) References Cited

U.S. PATENT DOCUMENTS

| | | | |
|---|---|---|---|
| 6,461,591 B1 | 10/2002 | Keller et al. | |
| 6,585,958 B1 | 7/2003 | Keller et al. | |
| 8,143,239 B2 * | 3/2012 | Govind et al. | 514/167 |
| 2003/0032632 A1 | 2/2003 | Cripps et al. | |
| 2007/0283814 A1 | 12/2007 | Mumbai et al. | |
| 2011/0150784 A1 * | 6/2011 | Bonelli et al. | 424/45 |

FOREIGN PATENT DOCUMENTS

| | | |
|---|---|---|
| CN | 1625392 | 6/2005 |
| EP | 0 372 777 A2 | 6/1990 |
| JP | 2002 521424 A | 7/2001 |
| JP | 2001 511160 A | 8/2001 |
| KR | 0154116 B1 | 11/1998 |

* cited by examiner

*Primary Examiner* — Robert A Wax
*Assistant Examiner* — Melissa Mercier
(74) *Attorney, Agent, or Firm* — Volpe and Koenig, P.C.

(57) ABSTRACT

The present invention is related to metered dose inhalation formulas and manufacturing process. The active pharmaceutical ingredient can be beta-2 agonists, corticosteroids, or a combination thereof. The inhalation formulas are homogenized suspensions with hydrofluoroalkane (HFA) propellant, minimal amount of ethanol and polyetheleneglycol (PEG) as suspending and particle size modifying agents.

16 Claims, 7 Drawing Sheets

Fig. 3

Particle Size Distribution and Stability of Bubesonide
(theoretical spray dosage of 180 mcg)

Fig. 7

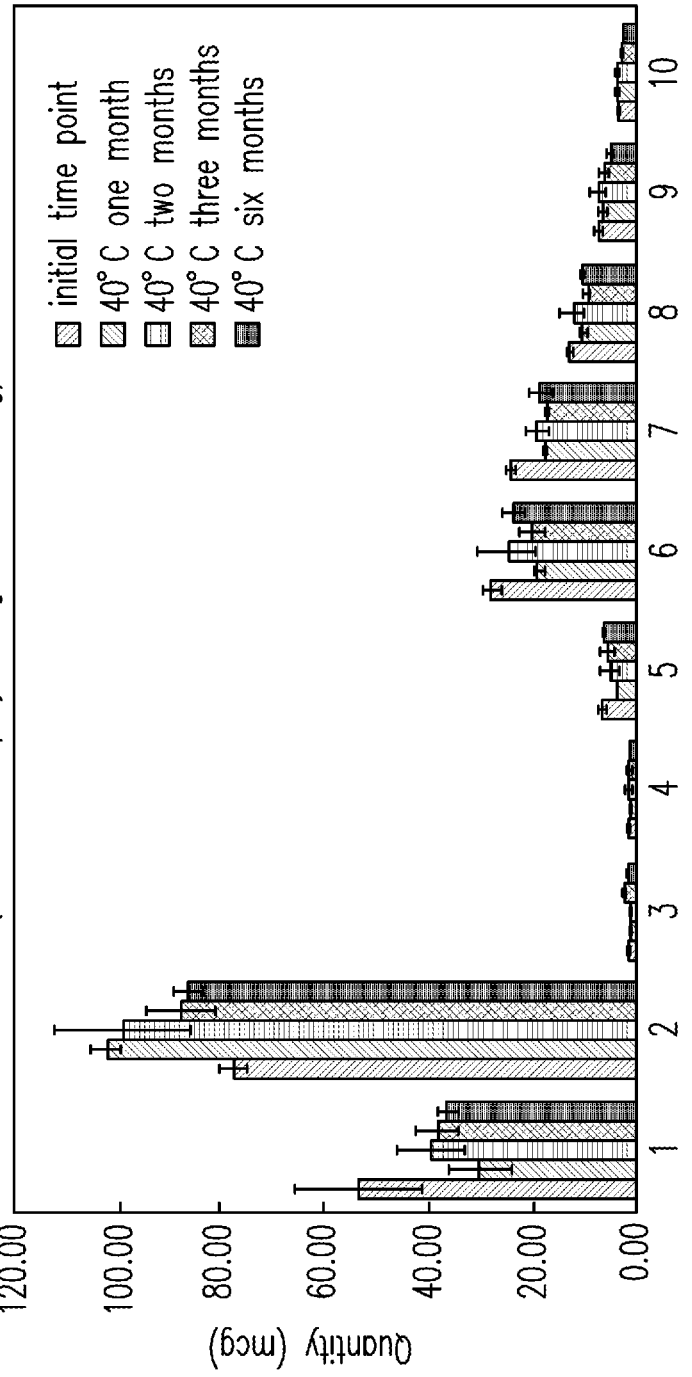

METHOD FOR PREPARING METERED DOSE SPRAYED INHALER FOR TREATING RESPIRATORY DISEASE

This application is a 35 U.S.C. §371 national stage application of PCT/CN2012/071129, which was filed Feb. 14, 2012 and claimed the benefit of CN20110239124.1, filed Aug. 19, 2011, both of which are incorporated herein by reference as if fully set forth.

FIELD OF THE INVENTION

The present invention provides a pressurized metered dose inhaler composition with pharmaceuticals and a preparing method thereof, wherein the pressurised metered dose inhaler is a medicine used for treating respiratory diseases such as asthma and chronic obstructive pulmonary disease.

BACKGROUND OF THE INVENTION

Pressurized metered dose inhaler (pMDI) can make the inhaled pharmaceuticals topically and rapidly present the activity of the medicine, and has lower systemic adverse reaction when compared with an oral drug. The pMDI and dry powder inhaler (DPI) are the most general administrations for asthma or chronic obstructive pulmonary disease (COPD), which are used to administer the composition being one selected from a group consisting of a corticosteroid drug, a beta-2 agonist, an anticholinergics and a combination thereof.

Since 1995, Company 3M developed a product of pMDI with chlorofluorocarbons (CFC) as a propellant, and the product has become most popular administration for treating asthma or COPD. Compared with the oral drug, the pMDI may present activity more rapidly and provide lower systemic adverse reaction of the medicine. Typical components for treating such diseases include a corticosteroid drug, a beta-2 agonist, an anticholinergics, or a pharmaceutical composition being a dose inhaler and consisting of the mentioned drugs.

In the 1970s, it is found that the propellant of CFC may result in environmental protection problems in destroying ozonosphere, and thus the CFC is confronted by the situation of global restriction. In the end of 1980s, a substitute product of the DPI was developed, but the substitute product can not completely replace the pMDI with the CFC propellant all along, since the product tends to suffer moisture and the patient needs enough speed of inhaling when using the product to be efficiently administered. Until now, Company Riker of 3M firstly develops a substitute propellant for replacing the CFC propellant, i.e. the propellant of hydrofluoroalkanes (HFA), which includes 1,1,1,2-tetrafluoroethane (HFA 134a, HFC 134a) or 1,1,1,2,3,3,3-heptafluoro-n-propane (HFC 227ea, HFC 227, HFA227). However, because there are some problems, such as techniques of preparation and drug safety, to be overcome, the first product of the formulation of HFA MDI did not enter into the market until 1996, and was booming in 2004, which results in the complete restriction on producing the CFC MDI after 2010.

In the U.S. Pat. Nos. 5,225,183, 5,439,670, 5,695,743, 5,766,573, 5,836,299 and 6,352,684 owned by Company Riker/3M, the patented formulation including HFA 134a has been disclosed. The formulation includes components of β-2-adrenergic agonists including such as salbutamol, corticosteroid such as beclomethasone dipropionate, adrenergic components, choline and anti-histamine or anti-inflammatory drugs, and uses 1-50% ethanol compound as a solubilizer, and the surfactant, which may be the derivatives such as oleic acid, polyethylene glycol 400(PEG 400) or Span, is added with a weight ratio less than 5%. In the U.S. Pat. No. 6,743, 413, HFA 134a and micronized drugs are used as main components without other excipients. The U.S. Pat. No. 5,776, 432 discloses that HFA 134a, HFA 227, or a combination thereof is used as the propellant, and 2%-12% ethanol is used as the solubilizer of the main drug component, beclomethasone 17, 21 dipropionate, without any surfactant.

The U.S. Pat. No. 5,474,759 owned by Company Schering discloses that HFA 227 is used as the propellant, and propylene glycol diester with a long chain is used as the surfactant, wherein the main components thereof include compounds such as albuterol, albuterol sulfate, beclomethasone dipropionate, or mometasone furoate.

In the U.S. Pat. Nos. 5,653,962, 5,658,549 and 5,744,123 owned by Company GSK, the patented formulation including HFA has been disclosed. The formulation includes main components such as salmeterol, salbutamol and fluticasone propionate, but does not have co-solvent, and uses the surfactant less than 0.001%. The subsequent patents thereof relate to the modification of drug delivery uniformity. The U.S. Pat. Nos. 6,315,173 and 6,510,969 relate to the improvement of the sprinkle-nozzle. The U.S. Pat. No. 6,479,035 uses Fluticasone and 7-20% alcohol as the solubilizer, and uses 0.5-3% glycerol or PEG as the surfactant. In the U.S. Pat. Nos. 5,736, 124, 5,817,293, 5,916,540, 5,922,306, 6,333,023, 6,200,549 and 6,222,339, the main component of formoterol has been disclosed, and 0.01-5% ethanol is adopted. The U.S. Pat. Nos. 6,303,103 and 6,238,647 disclose that salmeterol and anticholinergics are incorporated, and the excipient used thereby is less than 0.0001%. The U.S. Pat. No. 6,013,245 relates to beclomethasone and salbutamol, uses HFA 227 and does not use the surfactant. The U.S. Pat. No. 5,833,950 discloses beclomethasone, and uses HFA and the excipient less than 0.0001%.

Company Aeropharm has disclosed a patented formulation including HFA. The U.S. Pat. No. 5,891,419 discloses flunisolide with an addition of 0.5%-2% ethanol only. The U.S. Pat. No. 5,891,420 discloses triamcinolone acetonide with an addition of 1%-3% ethanol. The U.S. Pat. No. 6,458, 338 relates to a metered dose formulation with amino acid as the stabilizer. In the U.S. Pat. Nos. 6,447,750, 6,540,982, 6,540,983, 6,548,049 and 6,645,468, a metered dose formulation of a main component of a drug treating diabetes has been disclosed. The U.S. Pat. No. 6,464,959 discloses a metered dose formulation of a main component of a drug treating diabetes, which is incorporated with amino acid as the stabilizer.

The U.S. Pat. No. 6,004,537 owned by Company Baker Norton (now TEVA) discloses that HFA is used as the propellant, and uses 10%-40% (w/w) ethanol as the solubilizer to dissolve the main components of Budesonide and Formoterol.

The U.S. Pat. No. 6,123,924 owned by Fisons discloses main components such as $\beta_2$-receptor agonist: fenoterol hydrobromide, procaterol hydrochloride, salbutamol sulphate, terbutaline sulphate, anabolic steroid or steroid components; beclomethasone dipropionate, fluticasone propionate, tipredane, anti-histamine, anti-inflammation or acetyl-β-methylcholine bromide; cholinergic components: pentamidine isoethionate, tipredanene, docromil sodium, sodium cromoglycate, clemastine, budesonide and so on, which are distributed in HFA, and uses of polyvinylpyrrolidone (PVP) of 0.0000~10% w/w as the suspending agent and PEG 400-3000 as the lubricating agent.

The TW Patent Application No. 200303767 owned by Company Chiesi discloses formoterol superfine formulation, which includes 0.003-0.192% w/v of (R,R)-(±)-formoterol fumarate, wherein the combination technique of pressurized metered inhaler formulation is used and 10~20% ethanol and HCl are used to adjust pH value. It is emphasized that the ratio of particles equal to or less than 1.1 micrometer is larger than or equal to 30%. In the U.S. Pat. No. 7,223,381, the formulation is consisting of Budesonide, HFA propellant, and co-solvents of 13% ethanol and 0.2~2% glycerol.

The U.S. Pat. No. 6,638,495 owned by Company Nektar relates to a formulation combination technique where the phospholipid is used as the excipient to form a microstructure and materials having biological activities are distributed in the pressurized metered inhaler.

The U.S. Pat. No. 6,932,962 owned by Company Astra-Zeneca relates to HFA atomization dose including fatty acid or a salt thereof, bile salts, phospholipid or alkyl glycosides as the surfactant, wherein the amount of the ethanol used thereby can be 5-20%.

The U.S. Pat. No. 7,481,995 owned by University College Cardiff Consultants Limited relates to a HFA MDI formulation technique which uses amino acid as the suspending excipient.

When observing the mentioned prior arts based on the pressurized metered dose inhaler prescription, in addition to the medicine and HFA gas, the techniques can be classified according to using conditions of the ethanol as follows.

1). Without any additives, as represented by Company GSK, which provides the medicine completely presented by a suspending solution mode, while such medicine has a problem that it is more difficult to make the administration uniform.

2). Without the use of ethanol and a simple use of an excipient, such as PVP or propanediol bischloroacetate.

3). Large amount of ethanol (more than 10%), which would completely dissolve the medicine, and other excipients may be added or not. In this case, the advantage is good uniformity of the administration, and the disadvantage are possibly worse stability of the medicine and the rare delicacy of alcohol that has bad acceptance for patients.

4). Medium-low amount of ethanol (about 1% to 10%) collocated with other excipients, in which the medicine is in a condition of partially being dissolved and partially without being dissolved. It has bigger effect on the stability of the formula that the particle diameter of the medicine would be caused to change with passing of the preserving time.

5). Extreme-low amount of ethanol (about 0.2% to 2%), such as the formula of Company Valois. In this case, the advantage is the better stability of the medicine since it is in a suspending solution station without being dissolved, while the disadvantage is the bad uniformity of the administration and thus the assistance of other excipients may be needed. Moreover, it may have more difficulty in the manufacturing process.

Although Valois SAS has published the formula about Budesonide HFA MDI, which uses 0.1-5% of PEG 300 and 0.2-2% of ethanol (referring to Indian Journal of Pharmaceutical Science, Vol. 69, No. 5, P. 722-724, September-October 2007). However, in order to reduce the absorption of the container with the drug and increase the uniformity of the administration, the mentioned formula needs a use of a special surface-anodized container, such as a standard anodized aluminum canister, to be filled therewith. When it is used in an scale-up production or a general container, such as an aluminum canister, some problems about quality would be generated. Accordingly, when actually mass producing the mentioned formula in pharmaceutical industry, even though the formula components are the same, the differences of quality would still be resulted from different mixture orders of components and different ways and equipments of filling. The examples of the differences of quality are insufficient amount of the main component, cohering of the particles of the medicine, bad uniformity and so on. Particularly, the mentioned conditions would occur more easily when a product contains two kinds of main components, since there are differences of physical and chemical characteristics as well as ratio of content existing between said two main components. Therefore, a change of the producing process in combining the excipient with the contents of the formula, especially the application in mixture orders and homogenizing methods of the main components with the propellant and other excipients, may generate a pressurized metered dose inhaler with stable, safer and more efficacious qualities.

SUMMARY OF THE INVENTION

Lung is a tender tissue, and thus it is necessary to consider making harm to lung as low as possible when performing a pulmonary administration. Although surface cells of lung have motor fibers capable of excluding the inhaled foreign body, the excluding function is limited. Therefore, when designing the dose inhaler formula, it shall use excipients as few as possible or those with lower toxicity. Although the use of large amount of solubilizer may cause the product to present a better uniformity, the stability thereof would reduce correspondingly. Accordingly, the policy of HFA MDI formula is researched in the present invention, which intends to prepare a safe and efficient suspending solution dose with fewest excipient and solubilizer, to achieve good uniformity of administration and long stability of products, and to provide the patients with efficient dose (<5 micrometer) capable of entering into the lung. However, the reducing of amounts of the excipient and solubilizer in the patented HFA formula would easily reduce the stability and uniformity of the produced medicines, especially when the product contains two main components, such as beta-2 agonists and corticosteroids. Besides, large difference of dosages and different physical and chemical characteristics between the two main components would more easily result in the phenomenon of worse uniformity and stability of the main components in the dose. Moreover, because the main components cannot be uniformly mixed the excipient during the producing process of the suspending solution dose, the particles of medicine may easily cohere again, which results in the phenomenon of significant reducing of efficiently inhaled dose (fine particle dose).

The present invention provides a method of preparing a metered dose inhaler composition, comprising steps of:

a) mixing 0.05%-10% (w/w %) alcohol with a surfactant to form a first mixture;

b) dispersing a beta-2 agonist in the first mixture to form a second mixture;

c) adding a hydrofluoroalkane (HFA) propellant into the second mixture to form a third mixture;

d) dispersing a corticosteroid in the third mixture; and e) performing a filling step.

According to the mentioned concept, a stable and well-mixed suspending solution dose is formed in the present invention by using an inhaled medicine with proper producing process. The medicine includes a beta-2 agonist such as procaterol, salbutamol, formoterol and salmeterol, a corticosteroid such as budesonide, fluticasone, ciclesonide and beclomethasone, or a combination thereof. The hydrofluoroalkanes (HFA) propellant includes one of 1,1,1,2-tetrafluoroethane (HFA 134a, HFC 134a) or 1,1,1,2,3,3,3-heptafluoron-propane (HFC 227ea, HFC 227, HFA227), and the mentioned two HFA propellants may be mixed for use if necessary. The surfactant includes a polyethylene glycol (PEG) excipient for stabilizing the formula or lubricating the metering valve of container to prevent blocking, and the addition amount thereof is ranged from 0.01%-2.50% (w/w %), preferably 0.05%-1.50% (w/w %). Generally, the PEG having the mentioned concentration would not affect the solubility of the main components that results in reduction of stability. The PEG preferably has a molecular weight ranged from 100 to 6000, and in addition to the function of helping suspending, the PEG may be deemed as a corrector for particle diameter since the modification of the addition amount thereof may change the distribution of particle diameters. The ethanol absolute is added and the addition percent thereof is ranged from 0.05%-10.0% (w/w %), preferably 0.25%-2% (w/w %). With the mentioned concentration, the ethanol absolute may not only assistant in the dissolution of PEG, but also improve the phenomenon that the particles of the main component aggregate, which results from the HFA evaporated from the sprinkle-nozzle of the spray dose in the sprinkling moment. Furthermore, the surfactant, i.e. PEG 100-6000 molecular weight, used in the present invention is a commercially available product, and the needed viscosity can be adjusted by the amount of ethanol.

According to the mentioned concept, the present invention specifically provides a method of preparing a metered dose inhaler composition, comprising steps of:
  a) using 0.05%-10% (w/w %) alcohol as an alcohol solvent to be mixed with a surfactant to form a mixture solution;
  b) dispersing a beta-2 agonist in the mixture solution to form a uniform solution;
  c) adding HFA into the uniform solution;
  d) dispersing a corticosteroid in the uniform solution; and
  e) performing a freeze filling step or a pressure filling step.

In the producing process of the spray dose provided in the present invention, a step of uniformly dispersing PEG in HFA is an important step for controlling the uniformity of particles of the main component. Firstly, little amount of alcohol is uniformly mixed with PEG. Because the particles of drug of inhaling type are very fine, the particles are apt to aggregate. For uniformly dispersing the particles by PEG, it is necessary to perform the mixing step by ultrasonic vibration for forming a concentrated solution. The viscosity and volume of the mixture solution of alcohol and PEG may be changed with the quantity and property of the main component, while the amount thereof shall not be larger than 2% (w/w %) of the total amount of the formula. However, if the quantity of the main component medicine is more and the appeared volume is much larger than the volume of the mixture solution of alcohol and PEG, it is not necessary to mix the alcohol with PEG in advance. Next, the mentioned concentrated solution or the mixture solution of alcohol and PEG would be homogenizedly stirred with HFA to for a homogenized solution, and then the main component with large quantity is slowly added into and mixed with the homogenized solution. In the above-mentioned process, the order of adding the excipient and the way of mixing have significant effect. Particularly, when in a scale-up production, there are distinct improvements in the extent of uniformly dispersing of drug particles and the quantity of the main component medicine stained in the mixing tank. Finally, the freeze filling or pressure filling steps is performed.

DETAILED DESCRIPTION OF THE PREFERRED EMBODIMENT

Evaluation of Delivery Dose Uniformity:

The drug efficacy and safety of spray dose are affected by delivery dose uniformity, which includes:
  1. the suspending solution is dispersed uniformly and quickly when shaking the bottle;
  2. the uniformly suspending state is maintained at least 5 seconds after shaking; and
  3. the tolerance range of the sprinkle-nozzle of the spray (the USA Food and Drug Administration requires that a qualified range is that an average of a group of sprinkle-nozzles is the target value ±10%, and the respective sprinkle-nozzle is the target value ±15%).

For obtaining a credible uniformity test, a dose unit sampling apparatus (DUSA) as required by United States Pharmacopeia (USP) is used with glass fiber filter (1 μm). After performing a spray sampling under a required air-extracting flow rate (28.3 L/min), the quantities of drugs in the actuator (or mouthpiece) and the sampling/drug-collecting apparatus are measured respectively by high-efficient chromatography. The initial three sprayings, medium four sprayings and final indicated three sprayings of a bottle are respectively tested for a single dosage. The specification requires that the main components in a single spraying shall be less than 25% of the indicated dosage according to the requirements of the Pharmacopeia, and an average amount of the main components of all ten sprayings shall be less than 15% of the indicated dosage. Moreover, the delivery dose uniformity is evaluated under the conditions of 40, relative humidity 75% and maintenance of six-months storing period for facilitating the stability.

Evaluation of Particle Size Distribution:

For determining the condition of particle size distribution of the drugs, a spray sampling is performed under an air-extracting flow rate (30.0 L/min) required by USP, and the analysis of particle size of the drugs in the spray sampling is performed by using Next Generation Cascade Impactor. The distribution and changing circumstances of the particles in every level when using Next Generation Cascade Impactor are observed under the conditions of 40, relative humidity 75% and maintenance of six-months storing period for facilitating the stability, so as to evaluate the stability of the drug particles suspending in the formula solution.

The delivery dose uniformity is analyzed for the spray according to Formula Example I of the process of the spray dose provided in the present invention. As shown in FIG. 1 where Budesonide in the first spraying has an indicated dosage of 180 mcg, after the six-months test of facilitating stability (40 and relative humidity 75%), every bottle of the sprays including totally ten sprayings of delivery dosages is complying with the requirement that the main component in a single spraying shall be less than 25% of the indicated dosage and an average value shall be less than 15% of the indicated dosage according to the Pharmacopeia. As shown in FIG. 2 where Procaterol HCl in the first spraying has an indicated dosage of 10 mcg, after the six-months test of facilitating stability (40 and relative humidity 75%), every bottle of the sprays including totally ten sprayings of delivery dosages is complying with the requirement that the main component in a single spraying shall be less than 25% of the indicated dosage and an average value shall be less than 15% of the indicated dosage according to the Pharmacopeia.

As shown in FIG. 3 illustrating the analysis of particle size distribution, after the six-months test of facilitating stability (40 and relative humidity 75%), Budesonide is analyzed by using Next Generation Cascade Impactor for all levels, which include actuator, L-throat, Stage 1, Stage 2, Stage 3, Stage 4, Stage 5, Stage 6, Stage 7 and micro-orifice collector (MOC). There are no significant differences (ANOVA test, p>0.05) in quantity of Budesonide, when compared with that at initial time point, among the products in every level.

As shown in FIG. 4 illustrating the analysis of particle size distribution, after the six-months test of facilitating stability (40 and relative humidity 75%), Procaterol HCl is analyzed by using Next Generation Cascade Impactor for every level, and there are no significant differences (ANOVA test, p>0.05) in quantity of Procaterol HCl, when compared with that at initial time point, among the products in every level.

FIG. 5 illustrates the analysis of the delivery dose uniformity for Fluticasone in the spray of Formula Example VII, wherein the Fluticasone in the first spraying has an indicated dosage of 250 mcg. After the six-months test of facilitating stability (40 and relative humidity 75%), every bottle of the sprays including totally ten sprayings of delivery dosages is complying with the requirement that the main component in a single spraying shall not be over 25% of the indicated dosage and an average value shall not be over 15% of the indicated dosage according to the Pharmacopeia.

FIG. 6 illustrates the analysis of particle size distribution for Fluticasone in the spray of Formula Example VII. After the six-months test of facilitating stability (40 and relative humidity 75%), it is analyzed by using Next Generation Cascade Impactor for every level, and there are no significant differences (ANOVA test, p>0.05) in quantity of Fluticasone, when compared with that at initial time point, among the products in every level.

Figure 7:
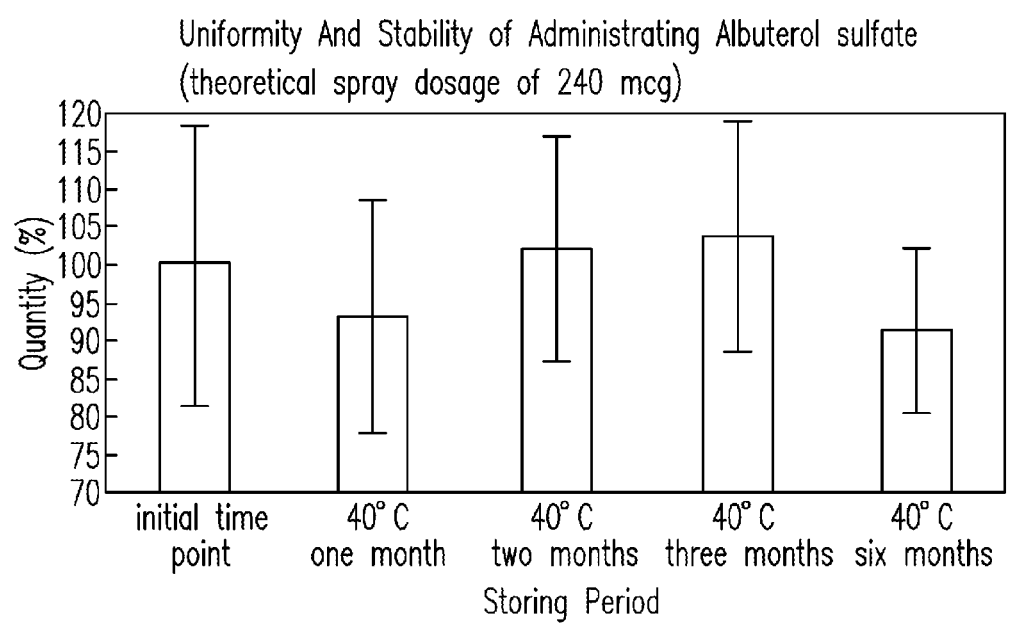

FIG. 7 illustrates the analysis of the delivery dose uniformity for Albuterol sulfate in the spray of Formula Example IX, wherein the Albuterol sulfate in the first spraying has an indicated dosage of 250 mcg. After the six-months test of facilitating stability (40 and relative humidity 75%), every bottle of the sprays which includes totally ten sprayings of delivery dosages is complying with the requirement that the main component in a single spraying shall not be over 25% of the indicated dosage and an average value shall not be over 15% of the indicated dosage according to the Pharmacopeia.

FIG. 8 illustrates the analysis of particle size distribution for Albuterol sulfate. After the six-months test of facilitating stability (40 and relative humidity 75%), it is analyzed by using Next Generation Cascade Impactor for every level, and there are no significant differences (ANOVA test, p>0.05) in quantity of Albuterol sulfate, when compared with that at initial time point, among the products in every level.

The object of the present invention is to promote the stability of amounts, the delivery dose uniformity and the stability of quality when producing the pressurized metered spray dose in the scale-up production. The formula applied to the producing process would deeply have industrial value especially when two main components having much differences in relative physical and chemical properties are combined in the product. Accordingly, the present invention is sought to be protected by operation of law. The "process of preparing metered dose inhaler for treating respiratory diseases" provided in the present invention will become more readily apparent to those ordinarily skilled in the art after reviewing the following examples. However, it is to be understood that the invention needs not be limited to the disclosed embodiments. The person skilled in the art could derive various embodiments according to the spirit of the disclosed embodiments, all of which shall belong to the scope of the appended claims in the present invention.

Process Example I

| | | |
|---|---|---|
| Procaterol HCl | 0.014% | W/W % |
| Budesonide | 0.252% | W/W % |
| HFA 227 | 98.984% | W/W % |
| ethanol absolute | 0.500% | W/W % |
| PEG 6000 | 0.250% | W/W % |
| Total Amount | 100.000% | W/W % |

Descriptions for Process

PEG 6000 is completely dissolved in the ethanol absolute to form a mixture solution, and then Procaterol HCl is poured into the mixture solution and dissolved by ultrasonic vibration to form an homogenized solution. After homogenizedly mixing HFA 227 with the homogenized solution, Budesonide is slowly added thereinto. Finally, freeze filling or pressure filling is performed.

Process Example II

| | | |
|---|---|---|
| Fluticasone propionate | 0.350% | W/W % |
| HFA 134a | 98.900% | W/W % |
| ethanol absolute | 0.500% | W/W % |
| PEG 400 | 0.250% | W/W % |
| Total Amount | 100.000% | W/W % |

Descriptions for Process

PEG 400 is completely dissolved in the ethanol absolute to form a mixture solution. After homogenizedly mixing HFA 134a with the mixture solution, Fluticasone is slowly added thereinto. Finally, freeze filling or pressure filling is performed.

Process Example III

| | | |
|---|---|---|
| Albuterol sulfate | 0.168% | W/W % |
| Fluticasone propionate | 0.322% | W/W % |
| HFA 134a | 97.510% | W/W % |
| ethanol absolute | 1.000% | W/W % |
| PEG 100 | 1.000% | W/W % |
| Total Amount | 100.000% | W/W % |

Descriptions for Process

PEG 100 is completely dissolved in the ethanol absolute to form a mixture solution, and then Albuterol sulfate is poured into the mixture solution and dissolved by ultrasonic vibration to form an homogenized solution. After homogenizedly mixing HFA 227 with the homogenized solution, Fluticasone propionate is slowly added thereinto. Finally, freeze filling or pressure filling is performed.

Process Example IV

| | | |
|---|---|---|
| Procaterol | 0.014% | W/W % |
| HFA 227 | 99.286% | W/W % |
| ethanol absolute | 0.500% | W/W % |
| PEG 2000 | 0.200% | W/W % |
| Total Amount | 100.000% | W/W % |

Descriptions for Process

PEG 2000 is completely dissolved in the ethanol absolute to form a mixture solution, and then Procaterol HCl is poured into the mixture solution and dissolved by ultrasonic vibration to form an homogenized solution. HFA 227 is homogenizedly mixed with the homogenized solution. Finally, freeze filling or pressure filling is performed.

Formula Example I

| Procaterol HCl | 0.014% | W/W % |
|---|---|---|
| Budesonide | 0.280% | W/W % |
| HFA 134a | 98.906% | W/W % |
| alcohol | 0.500% | W/W % |
| PEG 2000 | 0.300% | W/W % |
| Total Amount | 100.000% | W/W % |

Formula Example II

| Procaterol HCl | 0.014% | W/W % |
|---|---|---|
| Fluticasone propionate | 0.350% | W/W % |
| HFA 227 | 98.886% | W/W % |
| alcohol | 0.250% | W/W % |
| PEG 400 | 0.500% | W/W % |
| Total Amount | 100.000% | W/W % |

Formula Example III

| Albuterol sulfate | 0.168% | W/W % |
|---|---|---|
| Fluticasone propionate | 0.322% | W/W % |
| HFA 227 | 97.510% | W/W % |
| ethanol absolute | 1.500% | W/W % |
| PEG 400 | 0.500% | W/W % |
| Total Amount | 100.000% | W/W % |

Formula Example IV

| Procaterol | 0.014% | W/W % |
|---|---|---|
| HFA 134a | 97.986% | W/W % |
| alcohol | 1.000% | W/W % |
| PEG 100 | 1.000% | W/W % |
| Total Amount | 100.000% | W/W % |

Formula Example V

| Procaterol HCl | 0.014% | W/W % |
|---|---|---|
| Budesonide | 0.333% | W/W % |
| HFA 134a | 98.903% | W/W % |
| alcohol | 0.250% | W/W % |
| PEG 400 | 0.500% | W/W % |
| Total Amount | 100.000% | W/W % |

Formula Example VI

| Budesonide | 0.330% | W/W % |
|---|---|---|
| HFA 227 | 99.530% | W/W % |
| alcohol | 1.500% | W/W % |
| PEG 2000 | 0.500% | W/W % |
| Total Amount | 100.000% | W/W % |

Formula Example VII

| Fluticasone propionate | 0.351% | W/W % |
|---|---|---|
| HFA 227 | 97.899% | W/W % |
| alcohol | 1.500% | W/W % |
| PEG 6000 | 0.250% | W/W % |
| Total Amount | 100.000% | W/W % |

Formula Example VIII

| Procaterol HCl | 0.014% | W/W % |
|---|---|---|
| Ciclesonide | 0.286% | W/W % |
| HFA 227 | 98.950% | W/W % |
| alcohol | 0.500% | W/W % |
| PEG 100 | 1.000% | W/W % |
| Total Amount | 100.000% | W/W % |

Formula Example IX

| Albuterol sulfate | 0.396% | W/W % |
|---|---|---|
| HFA 134a | 96.604% | W/W % |
| alcohol | 2.500% | W/W % |
| PEG 6000 | 0.500% | W/W % |
| Total Amount | 100.000% | W/W % |

Formula Example X

| Albuterol sulfate | 0.168% | W/W % |
|---|---|---|
| Beclomethasone dipropionate | 0.286% | W/W % |
| HFA 134a | 96.546% | W/W % |
| alcohol | 1.500% | W/W % |
| PEG 100 | 1.500% | W/W % |
| Total Amount | 100.000% | W/W % |

Formula Example XI

| Procaterol HCl | 0.014% | W/W % |
|---|---|---|
| Beclomethasone dipropionate | 0.286% | W/W % |
| HFA 227 | 98.950% | W/W % |
| alcohol | 0.250% | W/W % |
| PEG 400 | 0.500% | W/W % |
| Total Amount | 100.000% | W/W % |

EMBODIMENTS

1. A method of preparing a metered dose inhaler composition, comprising steps of:
    a) mixing 0.05%-10% (w/w %) alcohol with a surfactant to form a first mixture;
    b) dispersing a beta-2 agonist in the first mixture to form a second mixture;
    c) adding a hydrofluoroalkane (HFA) propellant into the second mixture to form a third mixture;
    d) dispersing a corticosteroid in the third mixture; and
    e) performing a filling step.
2. A method of preparing a metered dose inhaler composition, comprising steps of:
    a) mixing 0.05%-10% (w/w %) alcohol with a surfactant to form a first mixture;
    b) dispersing a beta-2 agonist in the first mixture to form a second mixture;
    c) adding HFA into the second mixture to form a third mixture; and
    d) dispersing a corticosteroid in the third mixture.
3. A method of preparing a metered dose inhaler composition, comprising steps of:
    a) mixing 0.05%-0.25% (w/w %) alcohol with a surfactant to form a first mixture;
    b) dispersing a beta-2 agonist in the first mixture to form a second mixture; and
    c) adding HFA into the second mixture to form a third mixture.
4. A method of embodiment 1, wherein the corticosteroid includes one selected from a group consisting of budesonide, fluticasone, beclomethasone, ciclesonide, fluticasone propionate, beclomethasone dipropionate and a combination thereof.
5. A method of embodiment 1, wherein the beta-2 agonist includes one selected from a group consisting of albuterol, procaterol, formoterol, albuterol sulfate, procaterol hydrochloride, formoterol fumarate and a combination thereof.
6. A method of embodiment 1, wherein the alcohol solvent is ethanol absolute.
7. A method of embodiment 1, wherein the mixing step is performed by ultrasonic vibration.
8. A method of embodiment 5, wherein the alcohol solvent preferably has an addition percent ranged from 0.25%-2% (w/w %).
9. A method of embodiment 1, wherein the surfactant includes a polyethylene glycol (PEG) having a molecular weight ranged from 100 to 6000.
10. A method of embodiment 9, wherein the surfactant preferably has an addition percent ranged from 0.01%-2.5% (w/w %).
11. A method of embodiment 9, wherein the surfactant preferably has an addition percent ranged from 0.05%-1.5% (w/w %).
12. A method of embodiment 1, wherein the HFA propellant includes one of HFA 134a and HFA 227.
13. A method of embodiment 12, wherein the HFA propellant may include a combination of HFA 134a and HFA 227.
14. A metered dose inhaler composition prepared according to the method as claimed in embodiment 1, wherein the composition is used as one of an emergency drug for a subject suffering an asthma attack and a drug during an eccentric therapy for the subject, wherein the subject has one of asthma and chronic obstructive pulmonary disease, and the drug in the eccentric therapy is administrated to the subject when the subject is in a condition being one of before and after sleeping.

While the invention has been described in terms of what is presently considered to be the most practical and preferred embodiments, it is to be understood that the invention needs not be limited to the disclosed embodiments. On the contrary, it is intended to cover various modifications and similar arrangements included within the spirit and scope of the appended claims which are to be accorded with the broadest interpretation so as to encompass all such modifications and similar structures.

BRIEF DESCRIPTION OF THE DRAWINGS

FIG. 3 is a diagram illustrating the analysis of particle size distribution for Budesonide of Formula Example I.
1: actuator
2: L-throst
3: Stage 1+Stage 2
4: Stage 3
5: Stage 4
6: Stage 5
7: Stage 6+Stage 7+micro-orifice collector (MOC)

FIG. 7 is a diagram illustrating the analysis of the delivery dose uniformity for Albuterol sulfate of Formula Example IX.

FIG. 8 is a diagram illustrating the analysis of particle size distribution for Albuterol sulfate of Formula Example IX.
1: actuator
2: L-throst
3: Stage 1
4: Stage 2
5: Stage 3
6: Stage 4
7: Stage 5
8: Stage 6
9: Stage 7
10: micro-orifice collector (MOC)

Figure 1:
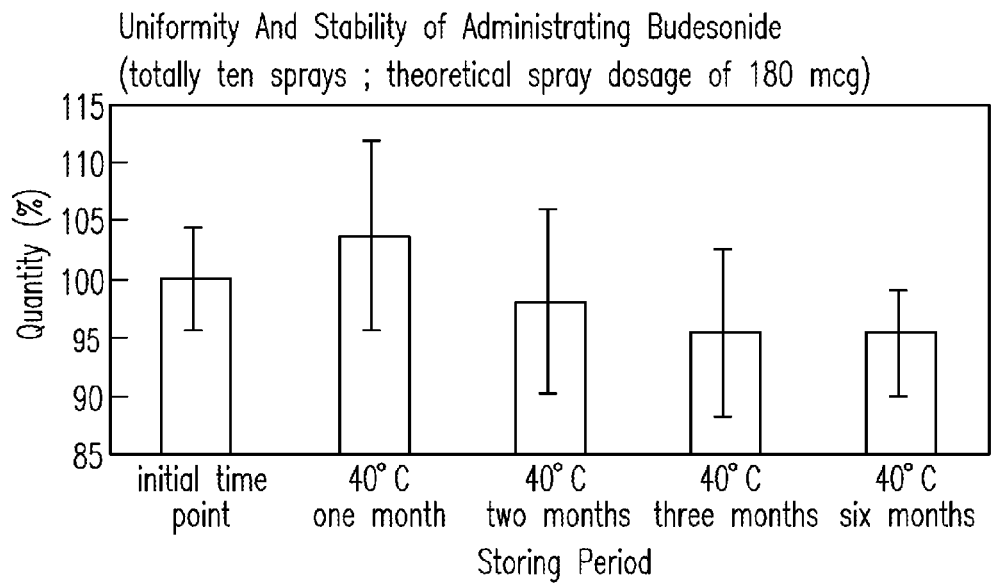
FIG. 1 is a diagram illustrating the analysis of the delivery dose uniformity for Budesonide of Formula Example I.
Figure 2:
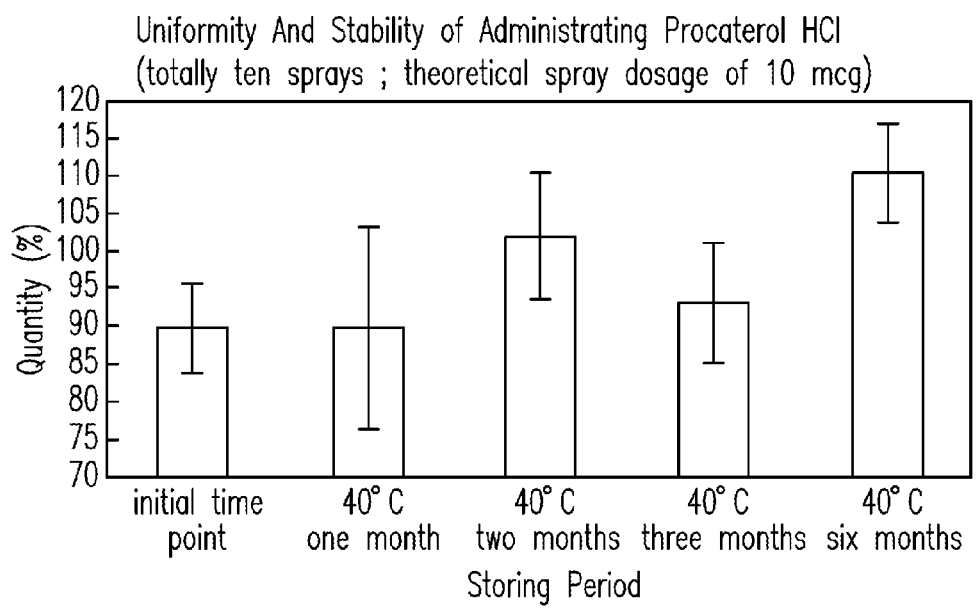
FIG. 2 is a diagram illustrating the analysis of the delivery dose uniformity for Procaterol HCl of Formula Example I.
Figure 4:
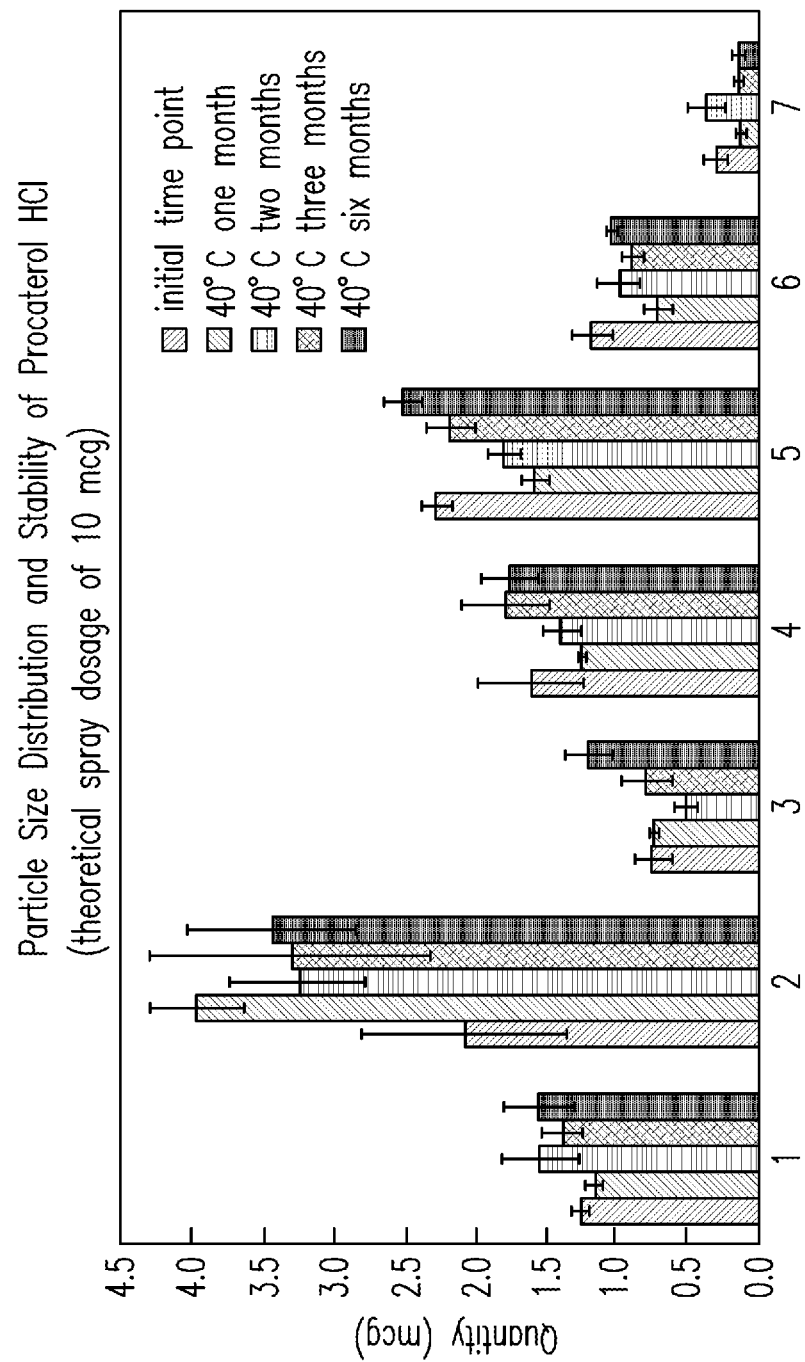
FIG. 4 is a diagram illustrating the analysis of particle size distribution for Procaterol HCl of Formula Example I.
1: actuator
2: L-throst
3: Stage 1+Stage 2
4: Stage 3
5: Stage 4
6: Stage 5
7: Stage 6+Stage 7+micro-orifice collector (MOC)
Figure 5:
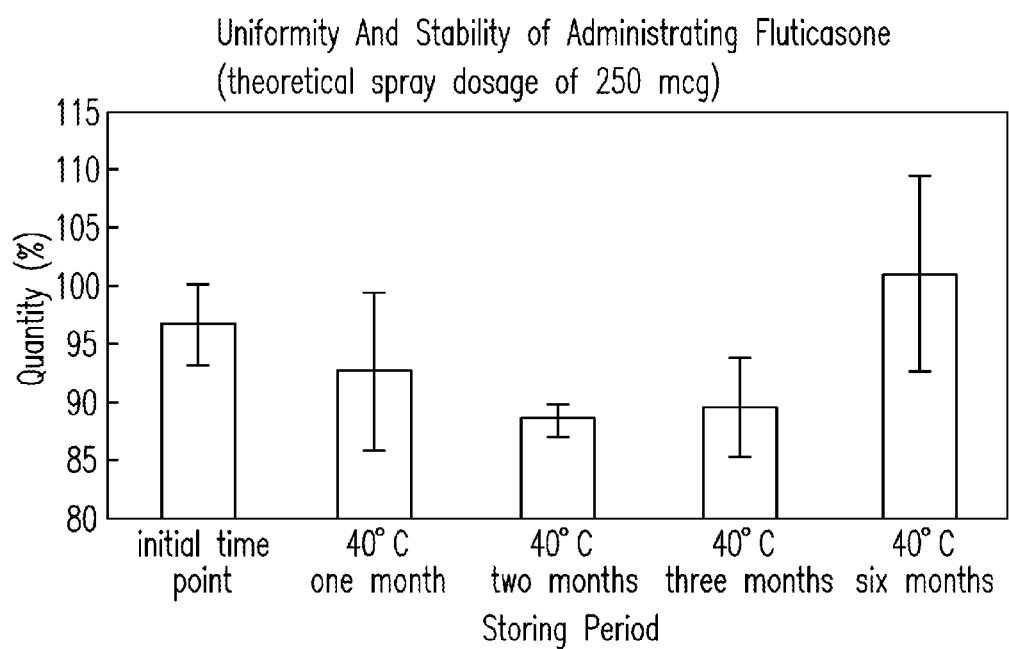
FIG. 5 is a diagram illustrating the analysis of the delivery dose uniformity for Fluticasone of Formula Example VII.
Figure 6:
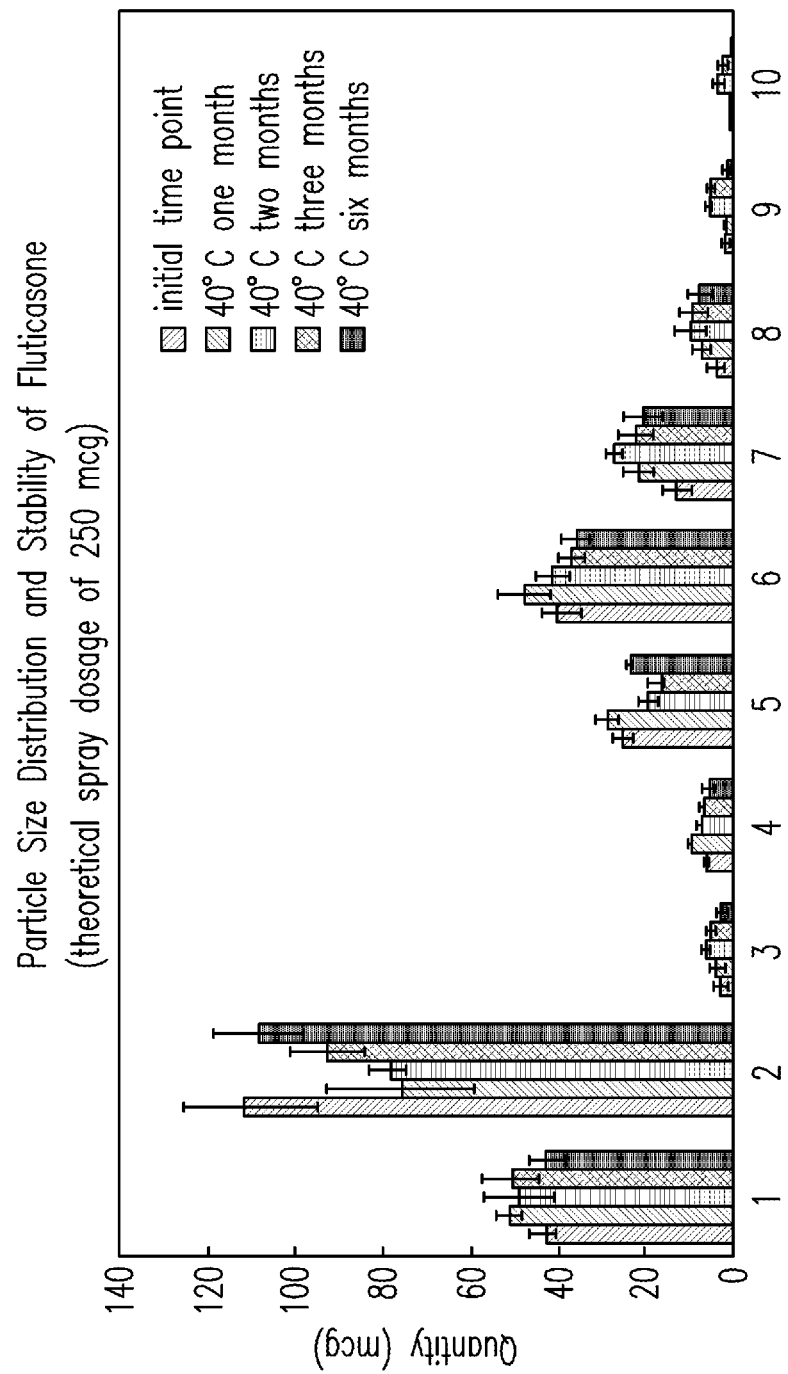
FIG. 6 is a diagram illustrating the analysis of particle size distribution for Fluticasone of Formula Example VII.
1: actuator
2: L-throst
3: Stage 1
4: Stage 2
5: Stage 3
6: Stage 4
7: Stage 5
8: Stage 6
9: Stage 7
10: micro-orifice collector (MOC)

What is claimed is:
1. A method of preparing a metered dose inhaler composition having a total weight, comprising steps of:
    a) mixing an alcohol with a surfactant to form a first mixture, wherein the alcohol has a content of 0.05%-10.0% (w/w %) of the total weight;
    b) adding and dispersing a beta-2 agonist in the first mixture to form a second mixture;
    c) adding a hydrofluoroalkane (HFA) propellant to the second mixture to form a third mixture;

d) adding and dispersing a corticosteroid in the third mixture; and e) performing a filling step.

2. A method as claimed in claim 1, wherein the corticosteroid includes one selected from a group consisting of budesonide, fluticasone, beclomethasone, ciclesonide, fluticasone propionate, beclomethasone dipropionate and a combination thereof.

3. A method as claimed in claim 1, wherein the beta-2 agonist includes one selected from a group consisting of albuterol, procaterol, formoterol, albuterol sulfate, procaterol hydrochloride, formoterol fumarate and a combination thereof.

4. A method as claimed in claim 1, wherein the alcohol ranges from 0.25%-2.0% (w/w %).

5. A method as claimed in claim 1, wherein the surfactant includes a polyethylene glycol (PEG) having a molecular weight ranging from 100 to 6000.

6. A method as claimed in claim 1, wherein the surfactant has a content of 0.01%-2.50% (w/w %) of the total weight.

7. A method as claimed in claim 1, wherein the HFA propellant includes at least one of HFA 134a and HFA 227.

8. A metered dose inhaler composition prepared according to the method as claimed in claim 1, wherein the composition is used as a medicament, wherein the subject suffers one of asthma and chronic obstructive pulmonary disease.

9. A method of preparing a metered dose inhaler composition having a total weight, comprising steps of:

a) mixing an alcohol with a surfactant to form a first mixture, wherein the alcohol has a content of 0.05%-10.0% (w/w %) of the total weight;

b) adding and dispersing a beta-2 agonist in the first mixture to form a second mixture;

c) adding a hydrofluoroalkane (HFA) propellant to the second mixture to form a third mixture; and d) adding and dispersing a corticosteroid in the third mixture to form the metered dose inhaler composition.

10. A method as claimed in claim 9, wherein the corticosteroid includes one selected from a group consisting of budesonide, fluticasone, beclomethasone, ciclesonide, fluticasone propionate, beclomethasone dipropionate and a combination thereof.

11. A method as claimed in claim 9, wherein the beta-2 agonist includes one selected from a group consisting of albuterol, procaterol, formoterol, albuterol sulfate, procaterol hydrochloride, formoterol fumarate and a combination thereof.

12. A method as claimed in claim 9, wherein the content of the alcohol ranges from 0.25%-2.0% (w/w %).

13. A method as claimed in claim 9, wherein the surfactant includes a polyethylene glycol (PEG) having a molecular weight ranging from 100 to 6000.

14. A method as claimed in claim 9, wherein the surfactant has a content of 0.01%-2.50% (w/w %) of the total weight.

15. A method as claimed in claim 9, wherein the HFA propellant includes at least one of HFA 134a and HFA 227.

16. A metered dose inhaler composition which is prepared according to the method as claimed in claim 9.

* * * * *